(12) United States Patent
Morris et al.

(10) Patent No.: US 8,417,322 B2
(45) Date of Patent: Apr. 9, 2013

(54) METHOD AND APPARATUS FOR DIAGNOSING BONE TISSUE CONDITIONS

(75) Inventors: Michael D. Morris, Ann Arbor, MI (US); Steven A. Goldstein, Ann Arbor, MI (US); Barbara R. McCreadie, Ann Arbor, MI (US); Tso-Ching Chen, Ann Arbor, MI (US)

(73) Assignee: Regents of the University of Michigan, Ann Arbor, MI (US)

( * ) Notice: Subject to any disclaimer, the term of this patent is extended or adjusted under 35 U.S.C. 154(b) by 1424 days.

(21) Appl. No.: 10/879,797

(22) Filed: Jun. 29, 2004

(65) Prior Publication Data
US 2005/0010130 A1  Jan. 13, 2005

Related U.S. Application Data

(60) Provisional application No. 60/484,198, filed on Jul. 1, 2003.

(51) Int. Cl.
  *A61B 5/00* (2006.01)
(52) U.S. Cl.
  USPC .......................................................... 600/477
(58) Field of Classification Search ................... 600/477
  See application file for complete search history.

(56) References Cited

U.S. PATENT DOCUMENTS

| | | | |
|---|---|---|---|
| 4,321,930 A | 3/1982 | Jobsis et al. | |
| 4,635,643 A | 1/1987 | Brown | |
| 4,986,273 A | 1/1991 | O'Neill et al. | |
| 5,139,025 A | 8/1992 | Lewis et al. | |
| 5,197,470 A | 3/1993 | Helfer et al. | |
| 5,293,872 A | 3/1994 | Alfano et al. | |
| 5,452,723 A | 9/1995 | Wu et al. | |
| 5,615,673 A | 4/1997 | Berger et al. | |
| 5,987,346 A * | 11/1999 | Benaron et al. | 600/407 |
| 5,991,653 A | 11/1999 | Richards-Kortum et al. | |
| 6,040,906 A | 3/2000 | Harhay | |
| 6,060,169 A | 5/2000 | Kuczynski et al. | |
| 6,070,583 A | 6/2000 | Perelman et al. | |

(Continued)

FOREIGN PATENT DOCUMENTS

| | | |
|---|---|---|
| EP | 0 761 161 A1 | 3/1997 |
| WO | WO 01/52739 A1 | 7/2001 |
| WO | WO-02/03857 | 1/2002 |
| WO | WO-2005/004714 | 1/2005 |

OTHER PUBLICATIONS

Paschalis et al., "FTIR Microspectroscopic Analysis of Human Iliac Crest Biopsies from Untreated Osteoporotic Bone", Calcif. Tissue Int., 61, pp. 487-492, 1997.*
International Search Report issued by ISA in PCT/US2004/020858 on Oct. 27, 2004.

(Continued)

*Primary Examiner* — Jonathan Cwern
(74) *Attorney, Agent, or Firm* — Marshall, Gerstein & Borun LLP

(57) ABSTRACT

In a method for diagnosing or helping to diagnose a bone tissue condition of a patient, a portion of bone tissue of the patient is irradiated using a light source. The bone tissue may be irradiated in vivo through the skin or via an incision, for example. Alternatively, a biopsy of the bone tissue may be irradiated. Then, spectral content information for light scattered, reflected, or transmitted by the bone tissue is determined, and is used, at least in part, to determine whether the patient has a bone tissue condition.

44 Claims, 4 Drawing Sheets

U.S. PATENT DOCUMENTS

| | | | |
|---|---|---|---|
| 6,072,180 | A | 6/2000 | Kramer et al. |
| 6,196,226 | B1 | 3/2001 | Hochman et al. |
| 6,213,958 | B1 | 4/2001 | Winder |
| 6,285,901 | B1 | 9/2001 | Taicher et al. |
| 6,353,753 | B1 | 3/2002 | Flock et al. |
| 6,370,422 | B1 | 4/2002 | Richards-Kortum et al. |
| 6,373,567 | B1 | 4/2002 | Wise et al. |
| 6,385,484 | B2 | 5/2002 | Nordstrom et al. |
| 6,445,767 | B1 | 9/2002 | Karellas |
| 6,490,339 | B2 | 12/2002 | Mitchell et al. |
| 6,574,490 | B2* | 6/2003 | Abbink et al. ............ 600/316 |
| 6,690,966 | B1 | 2/2004 | Rava et al. |
| 6,697,665 | B1 | 2/2004 | Rava et al. |
| 6,949,635 | B1* | 9/2005 | Kumar et al. ............ 536/23.1 |
| 2002/0002336 | A1* | 1/2002 | Marchitto et al. ......... 600/473 |
| 2002/0010400 | A1* | 1/2002 | Camacho et al. .......... 600/473 |
| 2002/0150938 | A1 | 10/2002 | Kneipp et al. |
| 2002/0156380 | A1 | 10/2002 | Feld et al. |
| 2002/0169379 | A1* | 11/2002 | Camacho et al. .......... 600/473 |
| 2003/0130579 | A1 | 7/2003 | McClane et al. |
| 2003/0191398 | A1* | 10/2003 | Motz et al. ............... 600/478 |
| 2004/0073120 | A1 | 4/2004 | Motz et al. |
| 2004/0186383 | A1 | 9/2004 | Rava et al. |
| 2005/0003376 | A1 | 1/2005 | Kneipp et al. |
| 2005/0031181 | A1 | 2/2005 | Bi et al. |
| 2005/0261568 | A1 | 11/2005 | Hular et al. |

OTHER PUBLICATIONS

P.A. West, et al., "Fourier Transform Infrared Spectral Analysis of Degenerative Cartilage: An Infrared Fiber Optic Probe and Imaging Study," *Applied Spectroscopy*, vol. 58, No. 4, pp. 376-381 (Apr. 2004).

T.E. Ciarelli, et al., "Variations in Three-Dimensional Cancellous Bone Architecture of the Proximal Femur in Female Hip Fractures and in Controls," *J. Bone and Mineral Res*. vol. 15, No. 1, pp. 166-175 (2000).

B. L. Riggs, et al., "Changes in Bone Mineral Density of the Proximal Femur and Spine with Aging," *J. Clin. Invest*. vol. 70, pp. 716-723 (1982).

A. Carden, et al., "Ultrastructural Changes Accompanying the Mechanical Deformation of Bone Tissue: A Raman Imaging Study," *Calcif. Tissue Int*., vol. 72, pp. 166-175 (published online Dec. 2002).

David B. Burr, et al., "Bone Microdamage and Skeletal Fragility in Osteoporotic and Stress Fractures," *J. Bone and Mineral. Res*. vol. 12, No. 1, pp. 6-15 (1997).

Richard Mendelsohn, et al., "IR Microscopic Imaging of Pathological States and Fracture Healing of Bone," *Applied. Spectroscopy* vol. 54, No. 8, pp. 1183-1191 (2000).

E.P. Paschalis, et al., "FTIR Microspectroscopic Analysis of Human Osteonal Bone," *Calcif. Tissue Int*. vol. 59, pp. 480-487 (1996).

C. Rey, et al., "Resolution-Enhanced Fourier Transform Infared Spectroscopy Study of the Environment of Phosphate Ion in the Early Deposits of a Solid Phase of Calcium Phosphate in Bone and Enamel and their Evolution with Age: 2. Investigations in the $v_3$ $PO_4$ Domain," *Calcif. Tissue Int*. vol. 49, pp. 383-388 (1991).

A.W. Adamson, *Physical Chemistry of Surfaces*, pp. 496-497, (4th Ed. John Wiley and Sons, New York, 1982).

J.W. Zhang, et al., "Mechanisms of Growth and Dissolution of Sparingly Soluble Salts; Mineral-Water Interface Geochemistry," in *Reviews Mineralogy: Mineral-Water Interface Geochemistry*, vol. 23, pp. 368-396 (M. Hochella, Jr. and A. White eds. 1990).

Ian R. Lewis, et al., "Fiber-optic Probes for Raman Spectrometry," in *Handbook of Vibrational Spectroscopy*, vol. 2, pp. 1587-1597 (John M. Chalmers & Peter R. Griffiths eds. 2002).

Matthias Otto, *Chemometrics: Statistics and Computer Application in Analytical Chemistry*, pp. 28-39 (1999).

Shoji Kaminaka et al., "Near-infrared multichannel Raman spectroscopy toward real-time in vivo cancer diagnosis," J. Raman Spectroscopy, vol. 33, issue 7, pp. 498-502 (Jul. 10, 2002).

L.M. Miller, et al., "Synchrotron Infrared Microspectroscopy: A New Techique for Probing the Chemical Composition of Bone and its Implications for Understanding Osteoarthritis," *National Synchrotron Light Source, 1997 Activity Report*, pp. 2-34 to 2-35, (1997), available at http://www.nsls.bnl.gov/newsroom/publications/activityreport/1997/2instrum.pdf.

Bakker et al., "In Vivo Detection of Dysplastic Tissue by Raman Spectroscopy," Analytical Chemistry, 72(24), pp. 6010-6018 (2000).

Bohic et al., "Characterization of the Trabecular Rat Bone Mineral: Effect of Ovariectomy and Bisphosphonate Treatment," Bone. 26(4), pp. 341-348 (2000).

Boivin et al., "Strontium Distribution and Interactions with Bone Mineral in Monkey Iliac Bone after Strontium Salt (S 12911) Administration," Journal of Bone & Mineral Research, 11(9) pp. 1302-11 (1996).

Carden, A., et al., "Raman Imaging of Bone Mineral and Matrix: Composition and Function," Proc. S.P.I.E., vol. 3608, pp. 132-138 (1999).

Carden, et al., "Application of vibrational spectroscopy to the study of mineralized tissues," J. Biomedical Optics, vol. 5, No. 3, pp. 259-268 (2000).

Cody, D.D., et al., "Femoral Strength is Better Predicted by Finite Element Models than QCT and DXA," Journal of Biomechanics, vol. 32, No. 10, pp. 1013-1020 (1999).

Das et al., "Time-resolved fluorescence and photon migration studies in biomedical and model random media," Rep. Prog. Physics vol. 60, pp. 227-292 (1997).

Hoffler, C.E., et al:, "Nanoindentation Test Parameters Alter Lamellar-Level Bone Mechanical Properties," submission to Journal of Biomechanical Engineering.

'McCreadie, B.R., et al., "Perspective: Biomechanics of Fracture: Is Bone Mineral Density Sufficient to Assess Risk?" Journal of Bone and Mineral Research, vol. 15, No. 12, pp. 2305-2308 (2000).

Nabiev et al., "Selective Analysis of Antitumor Drug Interaction with Living Cancer Cells is Probed by Surface-Enhanced Raman Spectroscopy," Biophys J. 19(6) pp. 311-316 (1991).

Paschalis et al., "FTIR Microspectroscopic Analysis of Human Iliac Crest Biopsies from Untreated Osteoporotic Bone," Calcified Tissue International, 61(6), pp. 487-492 (1997).

Pezzuti, J.A., et al., "Hyperspectral Raman Imaging of Bone Growth and Regrowth Chemistry," S.P.I.E. vol. 3261, pp. 270-276 (1998).

Tadrous, "Methods for Imaging the Structure and Function of Living Tissues and Cells," Oct. 12, 2002, available at http://www.bialith.com/Teaching/PathologyPG/BAMScHCInV.PDF.

Timlin, J.A., et al., "Spatial Distribution of Phosphate Species in Mature and Newly Generated Mammalian Bone by Hyperspectral Raman Imaging," Journal of Biomedical Optics, vol. 4, No. 1, pp. 28-34 (1999).

"Predicting When Bones May Break," The Whitaker Foundation News, (2000) www.whitaker.org/news.

Search Results from U.S. Appl. No. 09/765,989 dated Jun. 9, 2002.
Search Results from U.S. Appl. No. 09/765,989 dated Jan. 14, 2003.
Search Results from U.S. Appl. No. 09/765,989 dated Jan. 27, 2003.

O. Akkus et al., "Aging of microstructural compartments in human compact bone," J. Bone Miner. Res. 18:1012-1019 (2003).

J. Bandekar, "Amide Modes and Protein Conformation," Biochimica et Biophysica Acta 1120:123-143 (1992).

V. Bentolila et al., "Intracortical remodeling in adult rat long bones after fatigue loading," Bone 23:275-281(1998).

T.L. Bihan et al., "Determination of the Secondary Structure and Conformation of Puroindolines by Infrared and Raman Spectroscopy," Biochemistry 35: 12712-12722 (1996).

R.D. Bloebaum et al., "Determining mineral content variations in bone using backscattered electron imaging," Bone 20:485-590 (1997).

T.M. Boyce et al, "Cortical aging differences and fracture implications for the human femoral neck," Bone 14:769-78 (1993).

A. Boyde et al., "Effect of estrogen suppression on the mineralization density of iliac crest biopsies in young women as assessed by backscattered electron imaging," Bone 22:241-50 (1998).

A. Boyde A et al., "Mineral density quantitation of the human cortical iliac crest by backscattered electron image analysis: variations with age, sex, and degree of osteoarthritis," Bone 16:619-27 (1995).

J.R. Buchanan, "Assessment of the risk of vertebral fracture in menopausal women," J. Bone & Joint Surg. 69:212-218 (1987).

D.B. Burr et al., "Alterations to the en bloc basic fuchsin staining protocol for the demonstration of microdamage produced in vivo," Bone 17:431-433 (1995).

B.M. Bussian, "How to Determine Protein Secondary Structure in Solution by Raman Spectroscopy: Practical Guide and Test Case DNase I," Biochemistry 28:4271-4277 (1989).

Y.N. Chirgadze et al., "Infrared Spectra and Resonance Interaction of Amide I Vibration of the Antiparallel-Chain Pleated Sheet," Biopolymers 15:607-625 (1976).

Y.N. Chirgadze et al., "Infrared Spectra and Resonance Interaction of Amide I Vibration of the Parallel-Chain Pleated Sheet," Biopolymers 15:627-636 (1976).

K. Choi et al., "A comparison of the fatigue behavior of human trabecular and cortical bone tissue," J. Biomech. 25:1371-1381 (1992).

K. Choi et al., "The elastic moduli of human subchondral, trabecular, and cortical bone tissue and the size-dependency of cortical bone modulus," J. Biomech .23:1103-1113 (1990).

T.E. Ciarelli, et al., "Architectural and material contributions to fracture of the spine and proximal femur," Doctoral Dissertation, University of Michigan (1998).

N.J. Crane et al. "Spectral imaging of mouse skulls undergoing craniosynstosis," Proc. SPIE 4959:111-119 (2003).

R.D. Crofts et al., "Aging changes in osteon mineralization in the human femoral neck," Bone 15:147-52 (1994).

J.D. Currey, "The effect of porosity and mineral content on the Young's modulus of elasticity of compact bone," J. Biomech. 21:131-139 (1988).

B.G. Frushour et al.. "Raman spectroscopic study of mechanically deformed poly-L-alanine," Biopolymers 13:455-474 (1974).

D. Garfinkel et al., "Raman spectra of amino acids and related compounds," Am. Chem. Soc. 80:3818 (1958).

M. Grynpas, "Age and disease-related changes in the mineral of bone," Calcif. Tissue Int. 53:S57-S64 (1993).

M. Grynpas et al., "Subchondral bone in osteoarthritis," Calcif. Tissue Int. 49:20-26 (1991).

C.E. Hoffler et al., "Age, gender, and bone lamellae elastic moduli," J. Orthop. Res. 18:432-437 (2000).

T. Ichimura et al., "Local enhancement of coherent anti-Stokes Raman scattering by isolated gold nanoparticles," J. Raman Spectrosc 34:651-654 (2003).

G. R. Jordan et al., "Spatial clustering of remodeling osteons in the femoral neck cortex: A cause of weakness in hip fracture?" Bone 26:305-313 (2000).

J. Jowsey, "Age changes in human bone," Clin. Orthop. 17:210-218.

I. Katz et al., "Qualitative Bone Mineral Changes in Osteoporosis," 33rd Annual Meeting of the Orthopaedic Research Society, San Francisco, CA, p. 263 (1987).

V.J. Kingsmill, "Mineralisation density of human mandibular bone: quantitative backscattered electron image analysis," J. Anat. 192:245-256 (1998).

J.L. Kuhn et al., "Comparison of the trabecular and cortical tissue moduli from human iliac crests," J. Orthop. Res. 7:876-884 (1989).

R.J. Lakshmi et al., "Osteoradionecrosis (ORN) of the mandible: A laser Raman spectroscopic study," Appl. Spectroscopy 57:1100-1116 (2003).

P. L. Mente et al., "Experimental method for the measurement of the elastic modulus of trabecular bone tissue," J. Orthop. Res. 7:456-461 (1989).

M.D. Morris et al., "Bone microstructure deformation observed by Raman microscopy," Proc SPIE 4254:81-89 (2001).

M.D. Morris et al., "Effects of Applied Load on Bone Tissue as Observed by Raman Spectroscopy," Proc SPIE 4614:47-54 (2002).

M.D. Morris et al., "Raman microscopy of de novo woven bone tissue," Proc. SPIE 4254:90-96 (2001).

N. Otsu, "A threshold selection method from gray-level histograms," IEEE Trans. on Systems, Man and Cybernetics SMC-9:62-66 (1979).

J.T. Pelton et al., "Spectroscopic Methods for Analysis of Protein Secondary Structure," Anal. Biochem. 277:167-176 (2000).

S. A. Reid et al., "Changes in the mineral density distribution in human bone with age: image analysis using backscattered electrons in the SEM," J. Bone Mineral Res. 2:13-22 (1987).

V. Renugopalakrishnan et al.; "Non-uniform Triple Helical Structure in Chick Skin Type I Collagen on Thermal Denaturation: Raman Spectroscopic Study," Z. Naturforsch [C]53:383-88 (1998).

J. Y. Rho et al., "Young's modulus of trabecular and cortical bone material: ultrasonic and microtensile measurements," J. Biomech. 26:111-119 (1993).

B. Riemer, "Characterization of the architecture, tissue properties, and continuum behavior of aging trabecular bone," Orthopaedic Transactions 18:421-422 (1994).

B. L. Riggs et al., "Differential changes in bone mineral density of the appendicular and axial skeleton with aging: Relationship to spinal osteoporosis," J. Clin. Invest. 67:328-335 (1981).

P. Roschger et al., "Validation of quantitative backscattered electron imaging for the measurement of mineral density distribution in human bone biopsies," Bone 23:319-26 (1998).

P. Roschger et al., "Mineralization of cancellous bone after alendronate and sodium fluoride treatment: a quantitative backscattered electron imaging study on minipig ribs," Bone 20:393-97 (1997).

J.G. Skedros et al., "The meaning of graylevels in backscattered electron images of bone," J. Biomed. Materials Res. 27:47-56 (1993).

J.G. Skedros et al., "Influence of mineral content and composition on graylevels in backscattered electron images of bone," J. Biomed. Materials Res. 27:57-64 (1993).

C.P. Tarnowski et al., "Mineralization of Developing Mouse Calvaria as Revealed by Raman Microspectroscopy," J. Bone Miner. Res. 17:1-9 (2002).

J.A. Timlin et al., "Raman Spectroscopic Imaging Markers for Fatigue-Related Microdamage in Bovine Bone," Anal. Chem. 72:2229-2236 (2000).

J.A. Timlin et al., "Chemical microstructure of cortical bone probed by Raman transects," Applied Spectroscopy 53:1429-1435 (1999).

A. Torreggiani et al., "Interaction of Biotin and Biotinyl Derivatives with Avidin: Conformational Changes Upon Binding," J. Raman Spectroscopy 31:445-450 (2000).

P.R. Townsend et al., "Buckling studies of single human trabeculae," J. Biomech. 8:199-201 (1975).

Y.N. Wang et al., "Determination of Molecular Changes in Soft Tissues Under Strain Using Laser Raman Microscopy," J. Biomech. 33:483-486 (2000).

E. Wentrup-Byrne et al., "Fourier transform Raman microscopic mapping of the molecular components in a human tooth," J. Raman Spectroscopy 28:151-158 (1997).

International Search Report issed in PCT/US2004/044038, mailed on May 25, 2005.

Written Opinion issued in PCT/US2004/044038, mailed on May 25, 2005.

Akkus,O., el al., "Age-related changes in physiochemical properties of mineral crystals are related to impaired mechanical function of cortical bone," *Bone* 34: 443-453, 2004.

Burr, D.B., "Microdamage and bone fragility," *Current Opinion in Orthopaedics* .12:365-370, 2001.

Cummings, S.R., "Are Patients with Hip Fractures More Osteoporotic?" *American Journal of Medicine* 78:487-494, Mar. 1985.

International Preliminary Report on Patentability for International Application No. PCT/US2004/044038, Mar. 29, 2007.

Office Action for U.S. Appl. No. 10/944,518, dated Apr. 23, 2007.

International Preliminary Examination Report dated Jan. 3, 2006 in PCT/US2004/020858.

Smukler et al., "Analysis of Normal Murine Cartilage Using Raman Spectroscopy," Poster Session at Internal Medicine Research Day, Dept. of Internal Medicine, University of Michigan, Jun. 2003, 19 pages.

Awonusi et al., "Carbonate Assignment and Calibration in the Raman Spectrum of Apatite," Calcif. Tissue Int., vol. 81, pp. 46-52, 2007.

McCreadie et al., "Bone tissue compositional differences in women with and without osteoporotic fracture," Bone, vol. 39, pp. 1190-1195, 2006.

Mendelsohn et al., "Infrared Spectroscopy, Microscopy, and Microscopic Imaging of Mineralizing Tissues: Spectra-Structure Correlations from Human Iliac Crest Biopsies," J. Biomedical Optics, vol. 4, No. 1, pp. 14-21, 1999.

Rey et al., "Fourier Transform Infrared Spectroscopic Study of the Carbonate Ions in Bone Mineral During Aging," Calcif. Tissue Int., vol. 49, pp. 252-258, 1991.
Penel et al., "MicroRaman Spectral Study of the PO4 and CO3 Vibrational Modes in Synthetic and Biological Apatites," Calcif. Tissue Int., vol. 63, pp. 475-481, 1998.
Penel et al., "Composition of Bone and Apatitic Biomaterials as Revealed by Intravital Raman Microspectroscopy", Bone 36, pp. 893-901, 2005.
Shim et al., "Study of Fiber-Optic Probes for in Vivo Medical Raman Spectroscopy," Applied Spectroscopy, vol. 53, No. 6, pp. 619-627, 1999.
Shim et al., "Study of Fiber-Optic Probes for Vivo Medical Raman Spectroscopy", Applied Spectroscopy, vol. 53, No. 6, 1999.
Carden et al., "Ultrastructural Changes Accompanying the Mechanical Deformation of Bone Tissue: A Raman Imaging Study," Calcified Tissue Int'l, vol. 72, pp. 166-175 (2003).
Skoog et al., *Principles of Instrumental Analysis*, 4th ed., pp. 296-309 (Saunders College Publishing 1992).
Chen et al., "Bone tissue ultrastructural defects in a mouse model for osteogenesis imperfecta: a Raman spectroscopy study," Proc. of SPIE, vol. 5321, pp. 85-92 (2004).
Dehring et al., "Identifying Chemical Changes in Subchondral Bone Taken from Murine Knee Joints Using Raman Spetroscopy," Applied Spectroscopy, vol. 60, No. 10, pp. 1134-1141 (2006).
Pfefer et al., "Multiple-fiber probe design for fluorescence spectroscopy in tissue," Applied Optics, vol. 41, No. 22, pp. 4712-4721 (2002).
Motz et al., "Optical fiber probe for biomedical Raman spectroscopy," Applied Optics, vol. 43, No. 3, pp. 542-554 (2004).
Abstract of Boskey et al., "Fourier transform infrared microspectroscopic analysis of bones of osteocalcin-deficient mice provides insight into the function of osteocalcin," *Bone*, 23(3):187-96 (1998).
Behrend et al., "Identification of outliers in hyperspectral Raman image data by nearest neighbor comparison," *Appl. Spectrosc.*, 56:1485-1488 (2002).
Chen et al. "Effect of Hydrogen Peroxide Bleaching on Bone Mineral/Matrix Ratio," *Appl. Spectrosc.*, 56:1035-1037 (2002).
Crane et al., "Study of Localization of Response to Fibroblast Growth Factor-2 in Murine Calvaria Using Raman Spectroscopic Imaging," *Proc. SPIE*, 5321:242-249 (2004).
Finney et al., "Ultrastructural elastic deformation of cortical bone tissue probed by NIR Raman spectroscopy," *Proc. SPIE*, 5321:233-241 (2004).
InPhotonics, Technical Note #13, "Background Filtering in Fiber Optic Raman Sampling Probes," 1999, 2 pages.
International Preliminary Examination Report for Application No. PCT/US2004/044038, dated Mar. 20, 2007.
Kale et al., "Three-dimensional cellular development is essential for ex vivo formation of human bone," *Nature Biotechnology*, 18:954-958 (2000).
Kozloff et al., "Brittle IV Mouse Model for Osteogenesis Imperfecta IV Demonstrates Postpubertal Adaptations to Improve Whole Bone Strength," *J. Bone Miner. Res.*, 19:614-622 (2004).
Lin et al., "Bone metastatic LNCaP-derivative C42B prostate cancer cell line mineralizes in vitro," *The Prostate*, 47:212-221 (2001).
Morris et al., "Application of high pressure Raman spectroscopy to bone biomechanics," *Proc. SPIE*, 4958:88-97 (2003).

Morris et al., "Bone tissue ultrastructural response to elastic deformation probed by Raman spectroscopy," *Faraday Discuss.*,126:159-168 (2004).
Morris et al., "Compatibility of Staining Protocols for Bone Tissue with Raman Imaging," *Calcif. Tissue Internat.*, 74:86-94 (2004).
Morris et al., "Ramen Spectroscopy of early mineralization of normal and pathologic calvaria as revealed by. Raman spectroscopy," *Proc. SPIE*, 4614:28-39 (2002).
Morris et al., "Kerr-gated picosecond Raman spectroscopy and Raman photon migration of equine bone tissue with 400-nm excitation," *Proc. SPIE*, 5321:164-169 (2004).
Morris et al., "Raman Imaging as a Probe of Chemical and Biomechanical Properties of Bone Tissue," *Proc. SPIE*, 3918:2-8 (2000).
Morris et al., "Recent Developments in Raman and Infrared Spectroscopy and Imaging of Bone Tissue," *Spectroscopy*,18:155-163 (2004).
Office Action for U.S. Appl. No. 10/944,518, dated Feb. 28, 2008.
Office Action for U.S. Appl. No. 10/944,518, dated Jun. 1, 2009.
Office Action for U.S. Appl. No. 10/944,518, dated Oct. 2, 2007.
Office Action for U.S. Appl. No. 10/944,518, dated Sep. 30, 2008.
Office Action for U.S. Appl. No. 11/217,755, dated Jan. 30, 2008.
Office Action for U.S. Appl. No. 11/217,755, dated Jun. 1, 2009.
Office Action for U.S. Appl. No. 11/217,755, dated Sep. 29, 2008.
Pillay, "The Use of Fingernails as a Means of Assessing Bone Health: A Pilot Study," *Journal of Women's Health*, 14(4):339-344 (2005).
Rehman et al., "Structural Evaluation of Human and Sheep Bone and Comparison with Synthetic Hydroxyapatite by FT-Raman Spectroscopy," *J. Bio. Mat. Res.*, 29:1287-1294 (1995).
Shea et al., "Bone tissue fluorescence reduction for visible laser Raman spectroscopy," *Appl. Spectrosc*, 56:182-186 (2002).
Shim et al., "Study of Fiber-Optic Probes for Vivo Medical Raman Spectroscopy," *Applied Spectroscopy*, 53(6):619-627 (1999).
Smith et al., "Fourier Transform Raman Spectroscopic Studies of Human Bone," *J. Mat. Sci.*, 5:775-778 (1995).
Stewart et al., "Trends in early mineralization of Murine calvarial osteoblastic cultures. A Raman Microscopic Study," *J. Raman Spectrosc.*, 33:536-543 (2002).
Tarnowski et al., "Earliest Mineral and Matrix Changes in Force-Induced Musculoskeletal Disease as Revealed by Raman Microspectroscopic Imaging," *J. Bone Miner Res.*, 19:64-71 (2004).
Timlin et al., "Raman Spectroscopic Imaging Markers for Fatigue-Related Microdamage in Bovine Bone," *Anal. Chem.*, 72:2229-2236 (2000).
Walters et al., "A Raman and Infrared Spectroscopic Investigation of Biological Hydroxyapatite," *J. Inorg. Biochem.*, 39:193-200 (1990).
Widjaja et al., "Band-Target Entropy Minimization (BTEM) Applied to Hyperspectral Raman Image Data," *Appl. Spectrosc.*, 57:1353-1362 (2003).
Widjaja et al., "Thermal perturbations to bone mineral crystal structure studied by Raman and NMR spectroscopies," *Proc. SPIE*, 5321:223-232 (2004).
Ohsaki et al., "Mechanism of Bone Destruction Due to Middle Ear Chloesteatoma as Revealed by Laser-Raman Spectrometry," *American Journal of Otolaryngology*, vol. 9, 117-126, 1988.
European Official Action for Application No. 04 777 255.3-2319 dated Oct. 26, 2010.
Office Action for Japanese Application No. 2006-517769 mailed on Aug. 16, 2010.

* cited by examiner

METHOD AND APPARATUS FOR DIAGNOSING BONE TISSUE CONDITIONS

CROSS-REFERENCE TO RELATED APPLICATIONS

The present application claims the benefit of U.S. Provisional Application No. 60/484,198, filed Jul. 1, 2003, which is hereby incorporated by reference herein in its entirety for all purposes.

STATEMENT REGARDING FEDERALLY SPONSORED RESEARCH OR DEVELOPMENT

This invention was made with Government support under Grant numbers P30 AR46024, R01 AR34399, and R01 AR47969 awarded by the Public Health Service division of the Department of Health and Human Services. The Government may own certain rights in this invention.

FIELD OF THE DISCLOSURE

The present disclosure generally relates to medical diagnostic apparatus and methods, and more particularly to apparatus and methods that may be used to help diagnose conditions of bone tissue.

BACKGROUND

Osteoporosis is an important healthcare problem. It is estimated that 24 million Americans are affected by osteoporosis and that osteoporosis led to $13.8 billion in healthcare costs in 1995. The risk of dying from hip fracture complications is the same as the risk of dying from breast cancer. For Caucasian females over 50, the risk of hip, spine, or distal forearm fractures is 40%. Osteoporosis is currently defined as a condition in which bone mineral density is greater than two standard deviations below the mean of a young healthy population.

Current techniques for screening individuals for fracture susceptibility are relatively inaccurate and/or pose risks to the patient. For example, the present preferred technique for diagnosis of osteoporosis is dual X-ray absorption (DXA), which measures the amount of mineral in the bone. In some patients, however, a low mineral content does not appear to lead to an increased risk of fracture. Additionally, DXA requires that the patient is exposed to ionizing radiation.

SUMMARY

Methods and apparatus are provided for diagnosing or helping to diagnose a bone tissue condition of a patient. For example, a susceptibility to fracture of the bone tissue may be estimated. First, a portion of bone tissue of the patient is irradiated using a light source. The bone tissue may be irradiated in vivo through the skin or via an incision, for example. Alternatively, a biopsy of the bone tissue may be irradiated. Then, spectral content information for light scattered, reflected, or transmitted by the bone tissue is determined. The spectral content information is used, at least in part, to determine whether the patient has a bone tissue condition.

In one embodiment, an apparatus is provided that includes a light source, and a light receiver to receive light from a portion of bone tissue of a patient irradiated by the light source. Additionally, a spectrum analyzer is optically coupled to receive light received by the light receiver. Further, a computing device is communicatively coupled to the spectrum analyzer and is configured to generate diagnostic information indicative of whether the patient has a bone tissue condition based at least in part on spectral content information.

In another aspect, a method is provided in which a portion of bone tissue of a patient is irradiated using a substantially monochromatic light source. Then Raman spectra information for light scattered by the bone tissue is determined. Next, the Raman spectra information is used, at least in part, to determine a susceptibility to fracture of the bone tissue.

In yet another embodiment, an apparatus for determining bone tissue susceptibility to fracture includes a light source and a Raman probe to receive light scattered from a portion of bone tissue of a patient irradiated by the light source. A spectrum analyzer receives light collected by the Raman probe and determines Raman spectra information for the collected light. A computing device is configured to generate diagnostic information indicative of a susceptibility to fracture of the bone tissue based at least in part on the Raman spectra information.

BRIEF DESCRIPTION OF THE DRAWINGS

The features and advantages of the apparatus and methods described herein will be best appreciated upon reference to the following detailed description and the accompanying drawings, in which.

DETAILED DESCRIPTION

Diagnostic Apparatus

Figure 1:
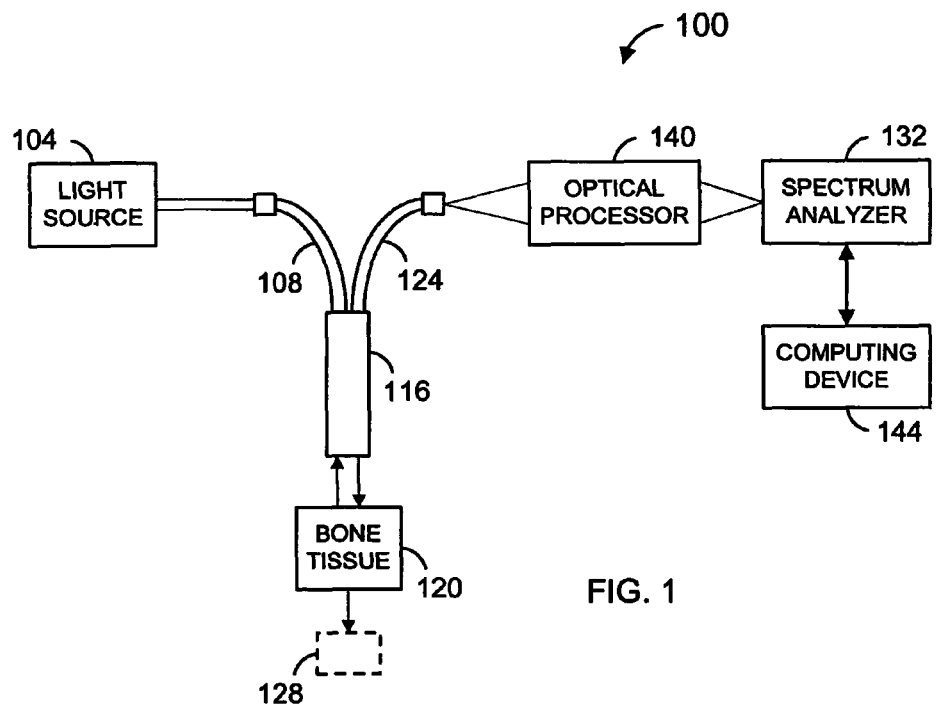
FIG. 1 is a block diagram of one embodiment of an apparatus for determining susceptibility to fracture.

FIG. 1 is a block diagram of an example apparatus 100 that may be used to help diagnose a condition of the bone tissue of a patient. For example, the apparatus 100 may be used to help diagnose osteoporosis, help estimate a susceptibility to fracture of the bone tissue, help diagnose a defect (e.g., osteogenesis imperfecta), help diagnose a nutritional disorder, or help diagnose other disorders related to bone tissue. The apparatus 100 may be used on a patient once, for example, or may be used multiple times over time to help track changes in the bone tissue.

The apparatus 100, which may be used for a Raman spectrometry analysis of a bone tissue or an infrared (IR) analysis of the bone tissue, includes a light source 104 optically coupled to at least one optical fiber 108. For Raman spectrometry, the light source 104 may comprise a laser, for example, that generates substantially monochromatic light. The optical fiber 108 is optically coupled to an optical probe 116. The optical probe 116 may be positioned proximate to a portion of bone tissue 120 from a patient, and may be used to irradiate the bone tissue 120 with the light generated by the light source 104.

In one embodiment, the optical probe 116 is also optically coupled to at least another optical fiber 124. In this embodiment, the optical probe 116 may be used to collect light scattered or reflected by the bone tissue 120 and to transmit the scattered light through the optical fiber 124. This embodiment may be used for Raman spectrometry or for "attenuated total reflection" IR spectrometry.

In another embodiment, another optical probe 128 may be positioned proximate to the portion of the bone tissue 120 such that the optical probe 128 can collect light transmitted by the bone tissue 120. The optical probe 128 may be optically coupled to the optical fiber 124 and can transmit the light transmitted by the bone tissue 120 through the optical fiber 124. This embodiment may be used for "line of sight" IR spectrometry.

The optical fiber 124 is optically coupled to a spectrum analyzer 132 via an optical processor 140 which may include one or more lenses and/or one or more filters. The spectrum analyzer 132 may include, for example, a spectrograph optically coupled to an array of optical detectors, and is communicatively coupled to a computing device 144.

Figure 2:
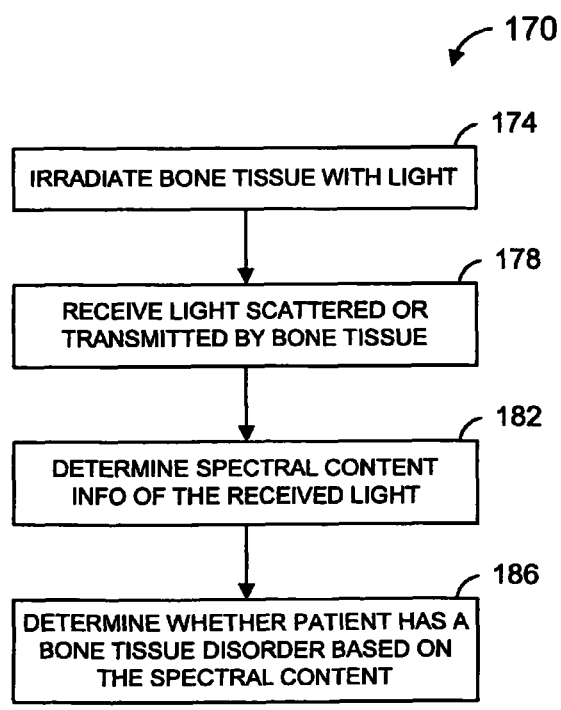
FIG. 2 is a flow diagram of one embodiment of a method for determining a susceptibility to fracture.

FIG. 2 is a flow diagram of a method for determining a condition related to the bone tissue of a patient. The method 170 may be implemented by an apparatus such as the apparatus 100 of FIG. 1, and will be described with reference to FIG. 1. At a block 174, a portion of bone tissue of a patient is irradiated with light. For example, the optical probe 116 may be used to irradiate the bone tissue 120 with light generated by the light source 104. In one embodiment, the bone tissue 120 may be irradiated non-invasively through the skin of the patient. In other embodiments, bone tissue 120 exposed by an incision, or removed as a biopsy, may be irradiated.

In some embodiments, bone tissue at or near a site presumed at risk for fracture (e.g., the hip) may be irradiated. Alternatively, bone tissue not at or near a site of presumed risk may be measured. For in vivo measurements, irradiation may occur at a site at which bone tissue is close to the skin. For example, the proximal diaphysis of the tibia may be irradiated. As biopsy measurements, an iliac crest biopsy could be irradiated as just one example.

At a block 178, light scattered, reflected, or transmitted by the bone tissue may be collected. For example, the optical probe 116 may collect light scattered by the bone tissue 120 (Raman spectrometry). As another example, the optical probe 116 may collect light reflected by the bone tissue 120 ("attenuated total reflection" IR spectrometry). Alternatively, the optical probe 128 may collect light transmitted by the bone tissue 120 ("line of sight" IR spectrometry). As with the optical probe 116, the optical probe 128 may collect light non-invasively through the skin of the patient. In other embodiments, the light may be collected via an incision or collected from an irradiated biopsy.

At a block 182, spectral content information associated with the collected light is generated. For example, the light collected by the optical probe 116 or the optical probe 128 may be provided to the spectrum analyzer 132 via the optical processor 140. The spectrum analyzer 132 may then generate spectral content information associated with the light received by the spectrum analyzer 132.

In Raman spectrometry, the collected light may include light at wavelengths shifted from the wavelength of the incident light. The spectrum of the collected light scattered from bone tissue (referred to hereinafter as the "Raman spectrum of the bone tissue") is indicative of the physico-chemical state of the bone tissue. The Raman spectrum of the bone tissue includes bands indicative of various components of the bone tissue including phosphate of bone mineral, carbonate of bone mineral, interstial water, residual water, hydroxide of the bone mineral, etc. Also included are bands indicative of various components of the collagen matrix of the bone tissue including amide I, hydroxyproline, proline, cross-links, etc. The wavelength at which a band is located is indicative of the component of the bone mineral or matrix to which it corresponds. The height and/or intensity of a band is indicative of the amount of the corresponding component of the bone tissue.

In IR spectrometry, the light generated by the light source 104 includes light at a variety of IR wavelengths. Some of the light at various wavelengths is absorbed by components of the bone tissue, and different components absorb different wavelengths. Thus, similar to the Raman spectrum of the bone tissue, in IR spectrometry, the spectrum of the collected light transmitted by the bone tissue (referred to hereinafter as the "IR spectrum of the bone tissue") includes bands indicative of components and structure of the bone tissue. Unlike in Raman spectrometry, however, the bands in the IR spectrum of the bone tissue are indicative of light absorbed by the bone tissue, rather than light scattered by the bone tissue. Nevertheless, the IR spectrum of the bone tissue is also indicative of the physico-chemical state of the bone tissue. As is known to those of ordinary skill in the art, the Raman spectrum of a bone tissue and an IR spectrum of the same bone tissue may provide indications of different components and/or different structure of the bone tissue.

At a block 186, it is determined whether the patient has a bone tissue disorder based on the spectral content information generated at block 182. For example, the computing device 144 may receive spectral content information from the spectrum analyzer 132. The computing device 144 may then generate an indication of whether the patient has a bone tissue disorder. As another example, the computing device 144 may generate an indication, based on the spectral content information generated at block the 182, that may be used by a physician to determine whether the patient has a bone tissue disorder. For example, the indication may be indicative of a susceptibility of the bone tissue of the patient to fracture. The bone tissue disorder may be, for example, osteoporosis, a genetic disorder (e.g., osteogenesis imperfecta), an acquired disorder, etc.

The determination of the block 186 may be based on additional factors. For example, the determination may be further based on one or more of an age of the patient, a height of the patient, a weight of the patient, a bone mineral density of the patient (e.g., determined using DXA), a family history of the patient, etc. Determining the estimate of susceptibility to fracture will be described in more detail below.

Blocks 174, 178, and 182 may optionally be repeated over a period of time (e.g, weeks, months, years) to generate spectral content information that reflects the condition of the bone tissue of the patient over the period of time. This spectral content information over the period of time may be used in the determination of block 186.

Estimating Susceptibility to Fracture

In one embodiment, the determination of block 186 comprises estimating a susceptibility of the bone tissue of the patient to fracture. Examples of techniques for estimating a susceptibility to fracture based on spectral content information are provided below. Many other techniques may be employed as well. In general, embodiments of methods for estimating susceptibility to fracture may vary according to the environment in which they are to be used. For example, different embodiments may be used in a clinical setting as compared to a laboratory setting because signal-to-noise ratios likely will be higher in the laboratory setting as compared to the clinical setting.

In some embodiments in which Raman spectrometry is employed, the area under a band or height of particular bands in the Raman spectrum of the bone tissue may be used to determine a susceptibility to fracture.

Amide I and amide III are observable in both IR and Raman spectrometry. Amide I and amide III spectra include information similarly indicative of the structure of collagen in the bone tissue, although amide I appears to produce more intense bands as compared to amide III. In Raman spectrometry, amide I of bone tissue is associated with a plurality of bands that can extend over much of the 1600 $cm^{-1}$ to 1700 $cm^{-1}$ region. For example, amide I of bone tissue is associated with a band approximately at 1650 $cm^{-1}$ and a band approximately at 1680 $cm^{-1}$ to 1690 $cm^{-1}$.

It is believed that the absence of collagen intrafibral crosslinks weakens bone tissue. The disruption or absence of collagen cross-links can result in changes to the relative intensities of the bands associated with amide I. For example, denaturing collagen to gelatin causes the high frequency shoulder associated with amide I to become more prominent. Additionally, the intrafibril cross-links in bone matrix collagen cause shifts in the proline bands (proline-2 and proline-3) from 1660 $cm^{-1}$ to 1663 $cm^{-1}$ and from 1670 $cm^{-1}$ to 1690 $cm^{-1}$ respectively. Research has shown that the 1690 $cm^{-1}$ band intensity in bone matrix increases relative to the intensity of the 1663 $cm^{-1}$ band when dehydrodihydroxylysinonorleucine, dehydrohydroxylysinonorleucine or dehydrohistindohydroxymerodesmosine cross-links are chemically reduced. Further research with fetal murine calvarial tissue has shown that the matrix amide I band in newly deposited tissue has a prominent shoulder at approximately 1690 $cm^{-1}$ that becomes smaller as the tissue ages and cross-links are formed.

Figure 3:
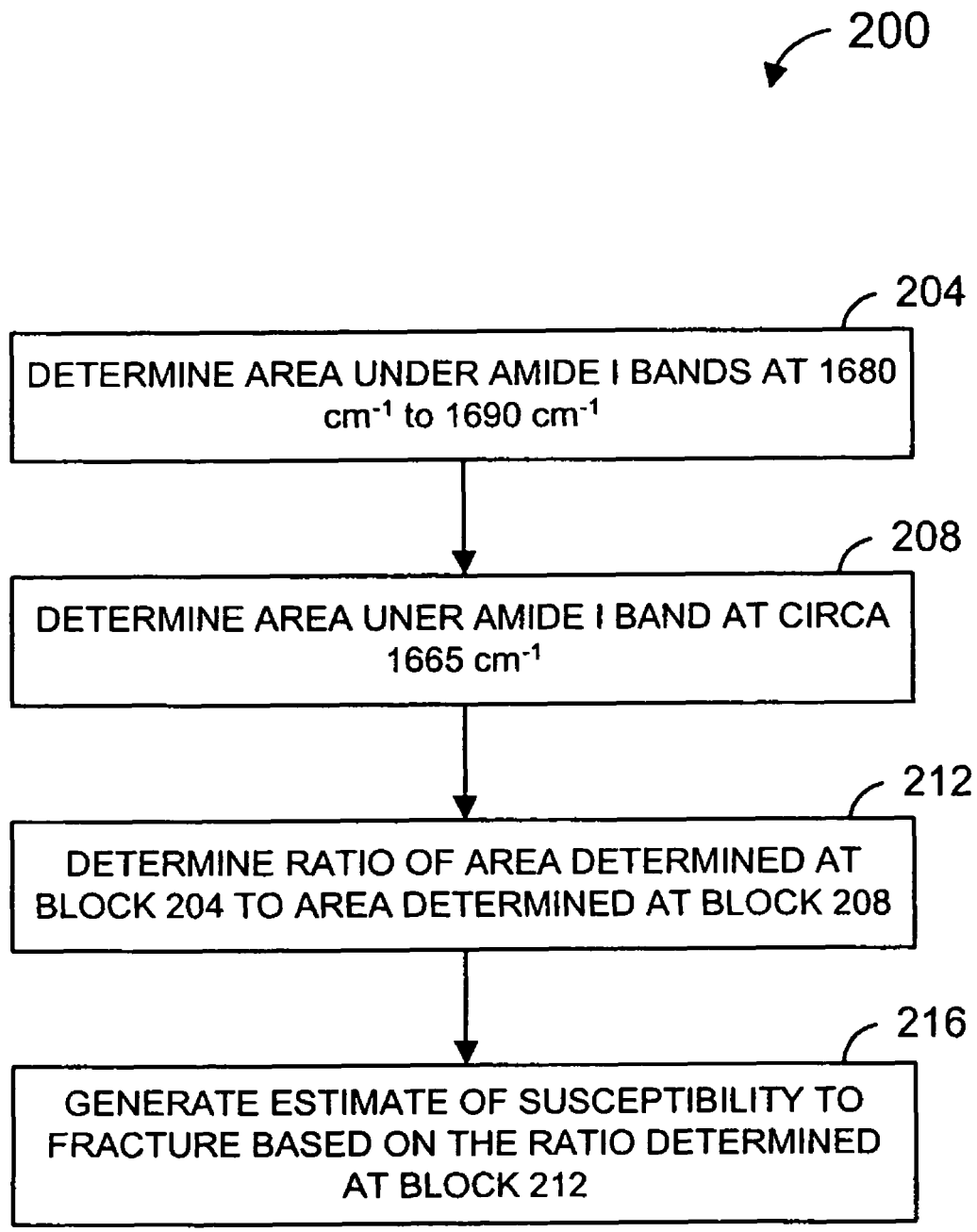
FIG. 3 is a flow diagram of one embodiment of a method for determining a susceptibility to fracture based on spectral content information.

FIG. 3 is a flow diagram illustrating one embodiment of a method for determining susceptibility to fracture based on areas of particular bands in a Raman spectrum of bone tissue. A similar technique may be employed for use with an IR spectrum of bone tissue.

At a block 204, an area of the amide I bands substantially between 1680 $cm^{-1}$ and 1690 $cm^{-1}$ is determined. Determining the area of these amide I bands may include curve fitting using a function such as a mixed Gaussian-Lorentzian function. Determining the area of the bands may also include measuring the area without curve fitting. For example, the area could be measured based on the raw data. As another example, the raw data could be filtered (e.g., with a smoothing filter), and the area could be measured based on the filtered data. In general, the areas under one or more bands may be determined using any of a variety of techniques, including known techniques. At a block 208, an area of the amide I band approximately at 1665 $cm^{-1}$ is determined. Determining the area of this amide I band may be performed in the same or similar manner as described with reference to block 204.

At a block 212, a ratio of the area determined at the block 204 with the area determined at the block 208 may be determined. Then, at a block 216, an estimate of the susceptibility to fracture of the bone tissue is determined based on the ratio determined at the block 212. Determining the estimate of the susceptibility to fracture may comprise determining in which of one or more sets of values the ratio falls. In one embodiment, the estimate of the susceptibility to fracture may comprise an indication of whether or not the bone tissue is susceptible to fracture. In other embodiments, the estimate of the susceptibility to fracture may additionally comprise an indication of one of a plurality of risk levels (e.g., high risk, increased risk, normal risk).

As described previously, the estimate of the susceptibility to fracture determined at the block 216 may be based on additional factors such as one or more of an age of the patient, a height of the patient, a weight of the patient, a bone mineral density of the patient, a family history of the patient, etc.

Figure 4:
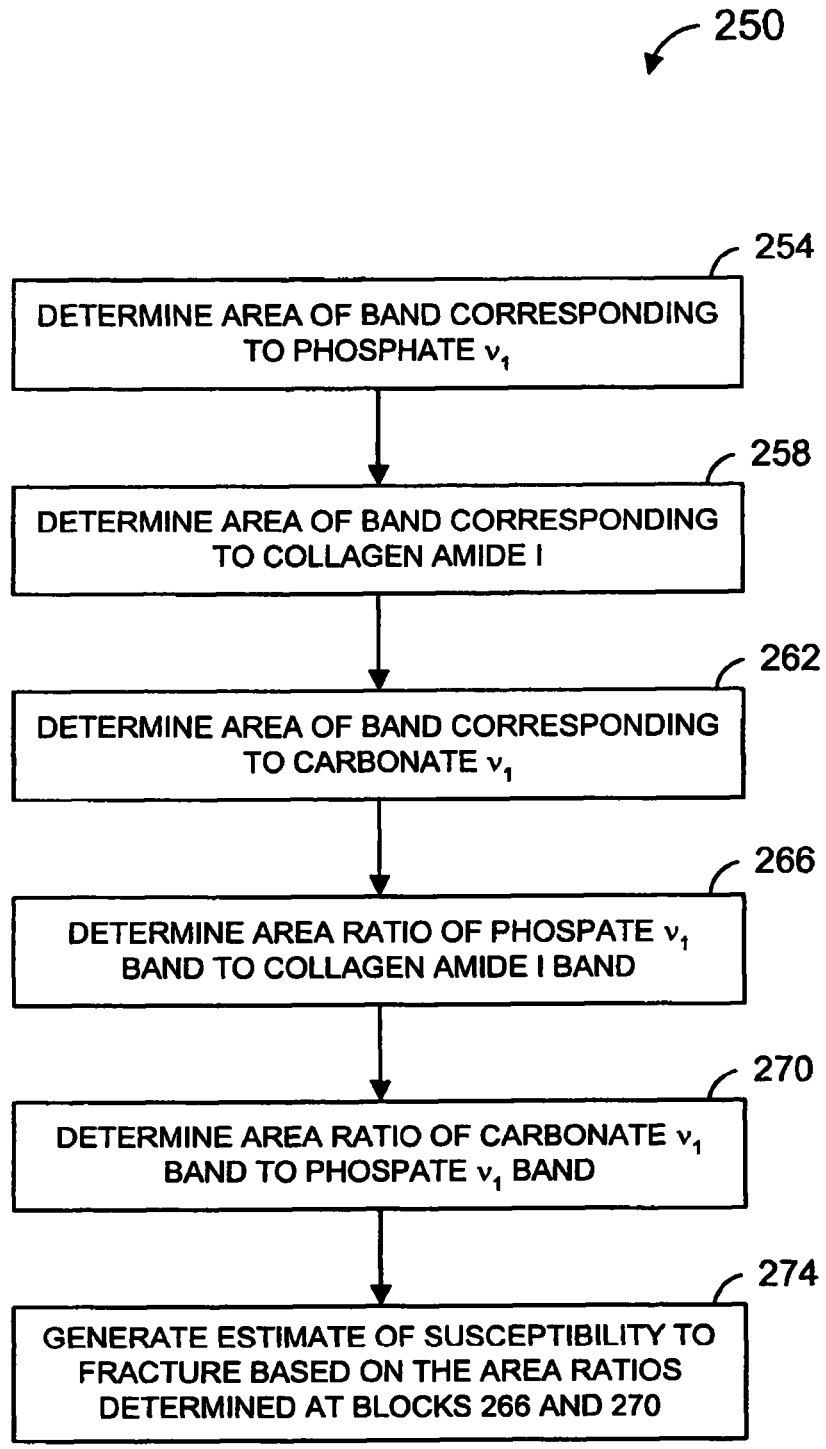
FIG. 4 is a flow diagram of another embodiment of a method for determining a susceptibility to fracture based on spectral content information.

FIG. 4 is a flow diagram illustrating another embodiment of a method for determining susceptibility to fracture based on areas of particular bands. At a block 254, an area of a band associated with phosphate $v_1$ and having a peak at approximately 957 $cm^{-1}$ and having a shoulder at approximately 940 $cm^{-1}$ is determined. Other phosphate bands could be used, although it is believed that the $v_1$ band is more intense than other phosphate bands. Determining the area of this phosphate $v_1$ band may include curve fitting to resolve the phosphate $v_1$ band into two components using a function such as a mixed Gaussian-Lorentzian function or some other suitable function. In general, the area of this band may be performed using any of a variety of techniques, including known techniques such as those described previously.

At a block 258, the area of the collagen amide I envelope (the plurality of bands between approximately 1600 $cm^{-1}$ to 1700 $cm^{-1}$) is determined. Other matrix bands could be used, for example bands indicative of hydroxyproline (853 $cm^{-1}$), proline (819 $cm^{-1}$), etc. Determining the area of the collagen amide I band may be performed in the same or similar manner as described previously. At a block 262, the area of the carbonate $v_1$ band (circa 1070 $cm^{-1}$) is determined. Determining the area of the carbonate $v_1$ band may be performed in the same or similar manner as described previously. Additionally, other carbonate bands could be used, although it is believed that the $v_1$ band is more intense than other carbonate bands.

At a block 266, a ratio of the area of the phosphate $v_1$ band to the area of the collagen amide I bands is determined. At a block 270, a ratio of the area of the carbonate $v_1$ band to the area of phosphate $v_1$ band is determined. It is believed that this ratio is a rough measure of the size and crystallinity of mineral crystals.

Figure 5:
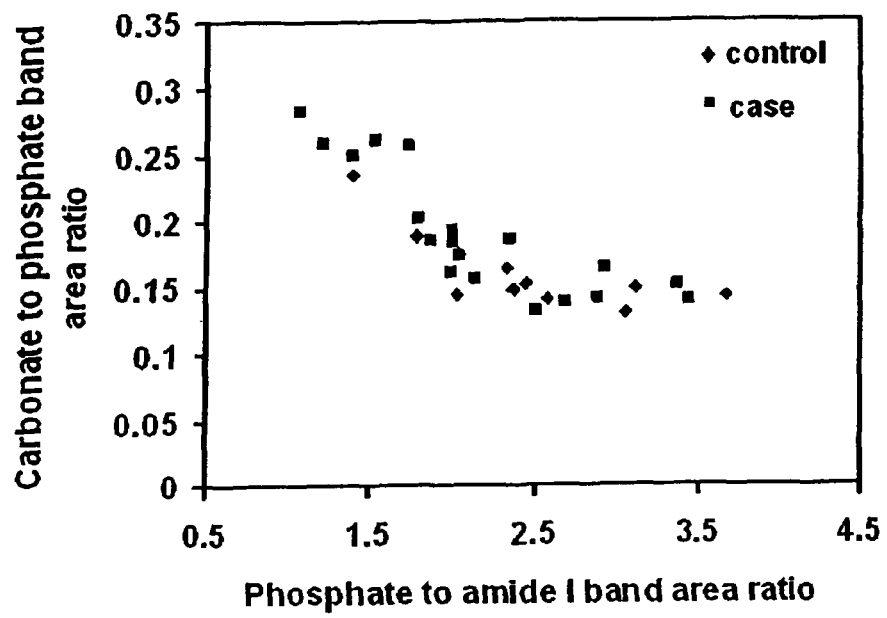
FIG. 5 is a chart showing measured spectral content information for a group of patients that suffered fractures and for a control group.
Figure 6:
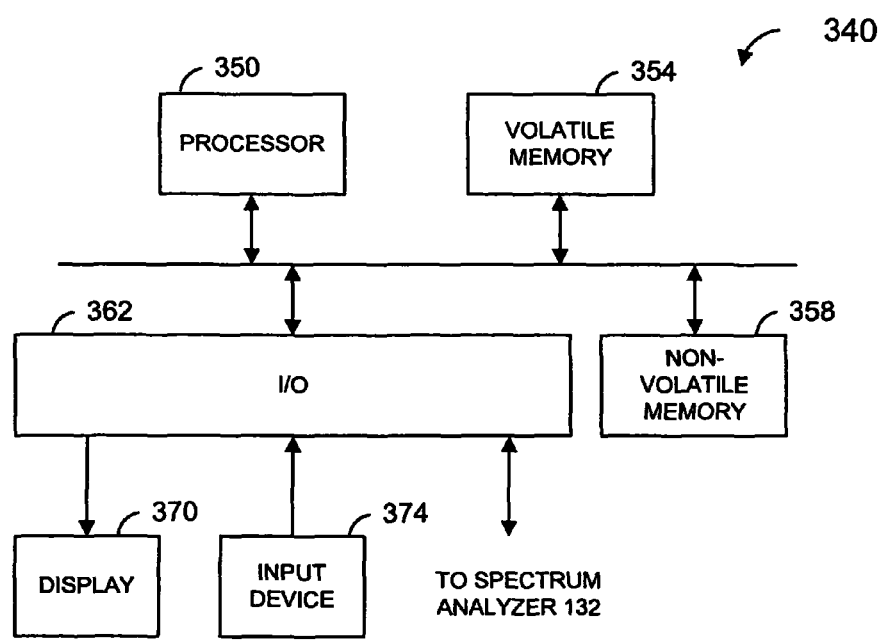
FIG. 6 is a block diagram of a computer that can be used with the apparatus of FIG. 1.

FIG. 5 is a plot of the above-described ratios determined from bone tissue taken from the proximal femur in the same location for each individual in a matched set of females. A control group included eleven individuals who had died without having a hip fracture. A fracture group included eighteen individuals who had sustained a hip fracture and were treated with arthroplasty. In the fracture group, those who had sustained fracture due to trauma such as automobile accidents or falls from a ladder were excluded. The control group and the fracture group were selected such that the age of the individuals and the bone volume fractions were similar between the two groups.

As can be seen in FIG. 5, a relationship exists between the carbonate/phosphate ratio and the phosphate/amide I ratio. As the phosphate/amide I ratio decreases, the carbonate/phosphate ratio at first generally remains approximately constant. As the phosphate/amide I ratio continues to decrease, the carbonate/phosphate ratio then tends to increase considerably. The fracture specimens tend to be concentrated at the low end of the phosphate/amide I ratio range, while the control specimens tend to be concentrated at the upper end of the phosphate/amide I ratio range. A low phosphate/amide I ratio and a high carbonate/phosphate ratio appear strongly associated with hip fracture. Student t-tests were conducted on the data illustrated graphically in FIG. 4. A comparison of the carbonate/phosphate ratios between the two groups (the fracture group and the control group) resulted in a p-value of 0.08.

A comparison of the phosphate/collagen ratios between the two groups resulted in a p-value of 0.28.

Referring again to FIG. 4, at a block 274, an estimate of the susceptibility to fracture of the bone tissue is determined based on the ratios determined at the blocks 266 and 270. Determining an estimate of the susceptibility to fracture may comprise determining whether the ratios determined at the blocks 266 and 270 fall within one or more sets of values. Additionally, in one embodiment, the estimate of the susceptibility to fracture may comprise an indication of whether or not the bone tissue is susceptible to fracture. In other embodiments, the estimate of the susceptibility to fracture may additionally comprise an indication of one of a plurality of risk levels (e.g., high risk, increased risk, normal risk).

The estimate of the susceptibility to fracture determined at the block 274 may be based on additional factors such as one or more of an age of the patient, a height of the patient, a weight of the patient, a bone mineral density of the patient, a family history of the patient, etc. Additionally, the estimate of the susceptibility to fracture determined at block 274 may be based on spectral content information taken over a period of time (e.g., weeks, months, years).

Other information in the IR spectrum or the Raman spectrum of the bone tissue can be used in addition to, or as an alternative, the information described above. For example, information related to bands other than those described above could be used. Additionally, information related to the width, shape (e.g., whether or not a band has "shoulders"), height, etc. of particular bands could be used in determining susceptibility to fracture. Additionally, more sophisticated analyses could be employed such as a cluster analysis.

In a study separate from the study associated with the data of FIG. 5, iliac crest biopsies were analyzed from ten subjects without fractures (mean age 56 years, range 43-70 years) and five subjects with osteoporotic fractures (mean age 63 years, range 50-72 years). In particular, for each specimen, trabecular and cortical regions were scanned using Raman spectroscopy and average carbonate/phosphate and phosphate/amide I band area rations were obtained for the trabecular and cortical regions. No corrections were made for multiple comparisions.

Both carbonate $v_1$/phosphate $v_1$ ratio and phosphate $v_1$/amide I ratio were higher in cortical than trabecular bone for all specimens (p=0.005 and p=0.01, respectively, paired t-tests). This may suggest that mineralized matrix chemistry differs between bone types due to, for example, a fundamental difference or a result of differing average tissue age. Chemical composition of cortical bone mineralized matrix appears to change with age, as demonstrated by a decrease in phosphate/amide I ratio (p=0.005, linear regression model). Neither carbonate $v_1$/phosphate $v_1$ ratio in cortical bone nor any measure in trabecular bone showed significant change with age. The phosphate $v_1$/amide I ratio in patients without fractures was greater in cortical than trabecular bone until age 55 (in all 6 subjects), but greater in trabecular bone in those 55 y or older (in all 4 subjects). In all 5 patients with fractures, the phosphate $v_1$/amide I ratio was greater in cortical bone. Thus, patients with fractures demonstrated the pattern seen in younger (under 55) non-fractured subjects, as opposed to the pattern of patients of similar age without fractures. It is possible that failure to alter mineralized matrix chemistry results in increased fracture risk. Another possibility is that the greater phosphate $v_1$/amide I ratio in cortical bone for patients with fractures, as compared to phosphate $v_1$/amide I ratio in the trabecular bone, was a result of the fracture. There may be other explanations as well for the differences in the relationship between phosphate $v_1$/amide I ratio in cortical bone and trabecular bone between patients with fractures and patients without fractures.

Comparing patients with fractures to patients without fractures, trabecular bone from patients with fractures had a lower phosphate $v_1$/amide I ratio (p=0.03, t-test). No differences appeared to be found in cortical bone or in carbonate $v_1$/phosphate $v_1$ ratio in trabecular bone. This lower mineral/matrix ratio (decreased mineral) in trabecular bone with patients with fractures may suggest a systemic increase in remodeling prior to or following fracture, and is likely demonstrated more clearly in trabecular bone because of its more rapid turnover. If this increase in remodeling occurs prior to fracture, chemical composition from iliac crest biopsy specimens may improve fracture risk assessment. The lower phosphate $v_1$/amide I ratio in trabecular bone for patients with fractures, however, could be a result of the fracture. There may be other explanations as well for the lower phosphate $v_1$/amide I ratio in trabecular bone for patients with fractures.

Yet another study was conducted that was designed to help understand whether, and how, the chemical composition of the bone extracellular matrix changes immediately after fracture. Raman spectroscopy was used to compare chemical composition between the fracture site and a location away from the fracture site. With this experimental model, it was assumed that there was originally no difference along the length of the bone. It was also assumed that there was little change far from the fracture site as a result of the fracture. Thus, differences in chemical composition found in this study between the fracture site and far from it may model changes in the chemical composition of the bone as a result of the fractures.

In this study, the tibiae of five mice were fractured in a controlled manner. One day later, the tibiae were dissected out and Raman spectra were obtained for cortical bone at/near the fracture site and approximately 2 mm from the fracture site (no trabecular bone was analyzed). Data from both locations were available for 4 limbs, each from separate animals.

The results indicated a decreased phosphate $v_1$/amide I ratio and increased carbonate $v_1$/phosphate $v_1$ ratio at the fracture site as compared to the site 2 mm away from the fracture. This data may suggest there is some change in the chemical composition of the bone extracellular matrix following fracture. It is important to note, however, that this assumes that there was no difference in chemical composition existed prior to the fracture between the two sites. It also assumes that there was little change at the site 2 mm away from the fracture site as a result of the fracture. There may be other explanations for why the study indicates decreased phosphate $v_1$/amide I ratio and increased carbonate $v_1$/phosphate $v_1$ ratio at the fracture site as compared to the site 2 mm away from the fracture.

Further Description of the Diagnosis Apparatus

In general, embodiments of apparatus for determining a bone tissue disorder may vary in design according to the environment in which they are to be used. For example, an apparatus to be used in a clinical setting may be designed to obtain spectrum information more quickly as compared to an apparatus to be used in a laboratory setting.

Referring again to FIG. 1, many types of light sources 104 may be employed. With regard to Raman spectrometry, a substantially monochromatic light source can be used. In general, near-infrared wavelengths provide better depth of penetration into tissue. On the other hand, as wavelengths increase, they begin to fall outside the response range of silicon photo detectors (which have much better signal-to-noise ratios than other currently available detectors). One example of a light source that can be used is the widely available 830 nanometer diode laser. This wavelength can penetrate at least 1 to 2 millimeters into tissue. Additionally, this wavelength is not absorbed by blood hemoglobin and is only weakly absorbed by melanin. If the bone tissue is to be exposed by incision, or if biopsied bone tissue is to be examined, other wavelengths may be employed. For example, a 785 nanometer diode laser could be used.

Many other wavelengths may be used as well. In general, a wavelength of a light source may be chosen based on various factors including one or more of a desired depth of penetration, availability of photo detectors capable of detecting light at and near the wavelength, efficiency of photo detectors, cost, manufacturability, lifetime, stability, scattering efficiency, penetration depth, etc. Any of a variety of substantially monochromatic light sources can be used, including commercially available light sources. For example, the article "Near-infrared multichannel Raman spectroscopy toward real-time in vivo cancer diagnosis," by S. Kaminaka, et al. (Journal of Raman Spectroscopy, vol. 33, pp. 498-502, 2002) describes using a 1064 nanometer wavelength light source with an InP/InGaAsP photomultiplier.

With regard to IR spectrometry, any of a variety of types of light sources can be used, including commercially available light sources. For example, light sources known to those of ordinary skill in the art as being suitable for analysis of bone tissues can be used.

With regard to the optical probe 116, any of variety optical probes can be used, including commercially available optical probes. For instance, the *Handbook of Vibrational Spectroscopy, Volume 2: Sampling Techniques,* 1587-1597 (J. Chalmers et al. eds., John Wiley & Sons Ltd. 2002) describes examples of fiber optic probes that can be used. For Raman spectrometry, optical probes designed for Raman spectrometry may be used. For example, any of a variety of commercially available fiber optic probes can be used. Some commercially available fiber optic probes include filters to reject Raman scatter generated within the excitation fiber and/or to attenuate laser light entering the collection fiber or fibers. Loosely focused light may help eliminate or minimize patient discomfort as compared to tightly focused light. As is known to those of ordinary skill in the art, loosely focused light may be achieved by a variety of techniques including multimode delivery fibers and a long focal length excitation/collection lens(es).

Existing commercially available fiber optic probes may be modified, or new probes developed, to maximize collection efficiency of light originating at depths of 1 millimeter or more below the surface of a highly scattering medium, such as tissue. Such modified, or newly developed probes, may offer better signal-to-noise ratios and/or faster data collection. The probe may be modified or may be coupled to another device to help maintain a constant probe-to-tissue distance, which may help to keep the system in focus and help maximize the collected signal.

If the bone is to be irradiated via an incision (and/or the light is to be collected via an incision), relay optics may be coupled to, or incorporated in, a needle. For example, two optical fibers or an "n-around-one" array could be used. In general, the size and the number of fibers should be appropriate to fit into a needle. The diameter of the excitation/collection lens or lenses used in such an embodiment could be small to help minimize the size of the incision. For example, lenses of diameters between 0.3 and 1 millimeter could be used. Lenses having larger or smaller diameters could be used as well. The lens(es) and or optical fibers could be incorporated into a hypodermic needle such as a #12 French type needle.

Additionally, a microprobe or microscope (e.g., a modified epi-fluorescence microscope) may be used instead of the optical probe 116 of FIG. 1. In this embodiment, the optical fiber 108 and/or the optical fiber 124 may be omitted.

The optical processor 140 may include one or more lenses for focusing the collected light. The optical processor 140 may also include one or more filters to attenuate laser light. Although shown separate from the spectrum analyzer 132, some or all of the optical processor 140 may optionally be a component of the spectrum analyzer 132.

The spectrum analyzer 132 may comprise a spectrograph optically coupled with a photo detector array. The photo detector array may comprise a charge coupled device, or some other photo detection device. For example, the article "Near-infrared multichannel Raman spectroscopy toward real-time in vivo cancer diagnosis," by S. Kaminaka, et al. (Journal of Raman Spectroscopy, vol. 33, pp. 498-502, 2002) describes using a 1064 nanometer wavelength light source with an InP/InGaAsP photomultiplier.

In another embodiment, the spectrum analyzer 132 may comprise one or more filters to isolate a plurality of wavelengths of interest. Then, one or more photo detectors (e.g., a CCD, an avalanche photodiode, photomultiplier tube, etc.) could be optically coupled to the output of each filter. A single detector could be used with a tunable filter (e.g., an interferometer, liquid crystal tunable filter, acousto-optic tunable filter, etc.) or if fixed passband filters (e.g., dielectric filters, holographic filters, etc.) are placed in front of the detector one at a time using, for example, a slider, filter wheel, etc. In general, any of a variety of spectrum analyzers could be used such as a Raman analyzer, an IR spectrum analyzer, an interferometer, etc.

The computing device 144 may comprise, for example, an analog circuit, a digital circuit, a mixed analog and digital circuit, a processor with associated memory, a desktop computer, a laptop computer, a tablet PC, a personal digital assistant, a workstation, a server, a mainframe, etc. The computing device 144 may be communicatively coupled to the spectrum analyzer 132 via a wired connection (e.g., wires, a cable, a wired local area network (LAN), etc.) or a wireless connection (a BLUETOOTH™ link, a wireless LAN, an IR link, etc.). In some embodiments, the spectral content information generated by the spectrum analyzer 132 may be stored on a disk (e.g., a floppy disk, a compact disk (CD), etc.), and then transferred to the computing device 144 via the disk. Although the spectrum analyzer 132 and the computer 144 are illustrated in FIG. 1 as separate devices, in some embodiments the spectrum analyzer 132 and the computing device 144 may be part of a single device. For example, the computing device 144 (e.g., a circuit, a processor and memory, etc.) may be a component of the spectrum analyzer 132.

FIG. 5 is a block diagram of an example computing device 144 that may be employed. It is to be understood that the computer 340 illustrated in FIG. 5 is merely one example of a computing device 144 that may be employed. As described above, many other types of computing devices 144 may be used as well. The computer 340 may include at least one processor 350, a volatile memory 354, and a non-volatile memory 358. The volatile memory 354 may include, for example, a random access memory (RAM). The non-volatile memory 358 may include, for example, one or more of a hard disk, a read-only memory (ROM), a CD-ROM, an erasable programmable ROM (EPROM), an electrically erasable programmable ROM (EEPROM), a digital versatile disk (DVD), a flash memory, etc. The computer 340 may also include an I/O device 362. The processor 350, volatile memory 354, non-volatile memory 358, and the I/O device 362 may be interconnected via one or more address/data buses 366. The computer 340 may also include at least one display 370 and at least one user input device 374. The user input device 374 may include, for example, one or more of a keyboard, a keypad, a mouse, a touch screen, etc. In some embodiments, one or more of the volatile memory 354, non-volatile memory 358, and the I/O device 362 may be coupled to the processor 350 via one or more separate address/data buses (not shown) and/or separate interface devices (not shown), coupled directly to the processor 350, etc.

The display 370 and the user input device 374 are coupled with the I/O device 362. The computer 340 may be coupled to the spectrum analyzer 132 (FIG. 1) via the I/O device 362. Although the I/O device 362 is illustrated in FIG. 5 as one device, it may comprise several devices. Additionally, in some embodiments, one or more of the display 370, the user input device 374, and the spectrum analyzer 132 may be coupled directly to the address/data bus 366 or the processor 350. Additionally, as described previously, in some embodiments the spectrum analyzer 132 and the computer 340 may be incorporated into a single device.

The previously described additional factors that may be used for diagnosing a bone tissue disorder (e.g., one or more of an age of the patient, a height of the patient, a weight of the patient, a bone mineral density of the patient, a family history of the patient, etc.) may be entered via the user input device 374, loaded from a disk, received via a network (not shown), etc. These additional factors may be stored in one or more of the memories 354 and 358. Additionally, previously measured spectral content information may be loaded from a disk, received via a network (not shown), etc., and stored in one or more of the memories 354 and 358.

A routine, for example, for estimating a susceptibility to fracture based on spectral content information may be stored, for example, in whole or in part, in the non-volatile memory 358 and executed, in whole or in part, by the processor 350. For example, the method 200 of FIG. 3 and/or the method 250 of FIG. 4 could be implemented in whole or in part via a software program for execution by the processor 350. The program may be embodied in software stored on a tangible medium such as CD-ROM, a floppy disk, a hard drive, a DVD, or a memory associated with the processor 350, but persons of ordinary skill in the art will readily appreciate that the entire program or parts thereof could alternatively be executed by a device other than a processor, and/or embodied in firmware and/or dedicated hardware in a well known manner. With regard to the method 200 of FIG. 3 and the method 250 of FIG. 4, one of ordinary skill in the art will recognize that the order of execution of the blocks may be changed, and/or the blocks may be changed, eliminated, or combined.

Although the method 200 of FIG. 3 and the method 250 of FIG. 4 were described above as being implemented by the computer 340, one or more of the blocks of FIGS. 3 and 4 may be implemented by other types of devices such as an analog circuit, a digital circuit, a mixed analog and digital circuit, a processor with associated memory, etc.

While the invention is susceptible to various modifications and alternative constructions, certain illustrative embodiments thereof have been shown in the drawings and are described in detail herein. It should be understood, however, that there is no intention to limit the disclosure to the specific forms disclosed, but on the contrary, the intention is to cover all modifications, alternative constructions and equivalents falling within the spirit and scope of the disclosure as defined by the appended claims.

What is claimed is:

1. A method for determining whether a patient has a condition related to bone tissue of the patient, the method comprising:
    irradiating a portion of bone tissue of the patient through skin of the patient using a substantially monochromatic light source;
    receiving light scattered from the portion of the bone tissue;
    determining Raman spectral content information associated with the received light including measuring a first ratio of a first spectral portion corresponding to amide to a second spectral portion corresponding to amide; and
    determining, based at least on the Raman spectral content information, including the first ratio, whether the patient has a bone tissue condition.

2. A method as defined in claim 1, wherein irradiating the portion of bone tissue of the patient using the substantially monochromatic light source comprises irradiating the portion of bone tissue of the patient using a substantially monochromatic light source that produces light having a wavelength substantially between 700 nanometers and 1100 nanometers.

3. A method as defined in claim 2, wherein irradiating the portion of bone tissue of the patient using the substantially monochromatic light source comprises irradiating the portion of bone tissue of the patient using a substantially monochromatic light source that produces light having a wavelength of substantially 830 nanometers.

4. A method as defined in claim 1, wherein irradiating the portion of bone tissue of the patient comprises irradiating the portion of bone tissue in vivo.

5. A method as defined in claim 1, wherein determining whether the patient has the bone tissue condition comprises determining whether the patient has at least one of a susceptibility to fracture, osteoporosis, a genetic disorder, and an acquired disorder.

6. A method as defined in claim 1, wherein determining whether the patient has a bone tissue condition comprises estimating a susceptibility to fracture of bone tissue of the patient based at least in part on the Raman spectral content information.

7. A method as defined in claim 6, wherein the Raman spectral content information includes a plurality of bands corresponding to received light at one or more wavelengths;
    wherein estimating the susceptibility to fracture includes determining at least one area or height of at least one band.

8. A method as defined in claim 7, wherein estimating the susceptibility to fracture further comprises fitting a curve to the at least one band.

9. A method as defined in claim 7, wherein determining the first ratio comprises:
    determining a first area or height of at least a first band;
    determining a second area or height of at least a second band; and
    determining the first ratio using the first area or height and the second area or height.

10. A method as defined in claim 9, wherein estimating the susceptibility to fracture further comprises estimating the susceptibility to fracture based on the first ratio.

11. A method as defined in claim 9, wherein estimating the susceptibility to fracture further comprises:
   determining a third area or height of at least a third band;
   determining a second ratio of the third area or height and the first area or height.

12. A method as defined in claim 11, wherein estimating the susceptibility to fracture further comprises estimating the susceptibility to fracture based on the first ratio and the second ratio.

13. A method as defined in claim 6, wherein estimating the susceptibility to fracture further comprises estimating the susceptibility to fracture further based at least in part on at least one of an age of the patient, a height of the patient, a weight of the patient, a bone mineral density of the patient, and a family history of the patient.

14. A method as defined in claim 1, wherein determining whether the patient has a bone tissue condition comprises determining whether the patient has a bone tissue condition further based at least in part on at least one of an age of the patient, a height of the patient, a weight of the patient, a bone mineral density of the patient, and a family history of the patient.

15. A method as defined in claim 1, wherein the first spectral portion and the second spectral portion each correspond to amide I.

16. A method as defined in claim 15, wherein the first spectral portion is at 1680 $cm^{-1}$ to 1690 $cm^{-1}$;
   wherein the second spectral portion is at 1665 $cm^{-1}$.

17. A method as defined in claim 1, wherein determining Raman spectral content information associated with the received light comprises measuring a second ratio of a first spectral portion corresponding to carbonate to a second spectral portion corresponding to phosphate; and
   wherein determining whether the patient has the bone tissue condition is further based on the second ratio.

18. A method as defined in claim 17, wherein the first spectral portion corresponds to carbonate $v_1$; and
   wherein the second spectral portion corresponds to phosphate $v_1$.

19. A method as defined in claim 18, wherein the first spectral portion is at 1070 $cm^{-1}$; and
   wherein the second spectral portion is at 957 $cm^{-1}$ with a shoulder at 940 $cm^{-1}$.

20. A method as defined in claim 17, wherein determining Raman spectral content information associated with the received light comprises measuring a third ratio of a third spectral portion corresponding to phosphate to a fourth spectral portion corresponding to amide; and
   wherein determining whether the patient has the bone tissue condition is further based on the third ratio.

21. A method as defined in claim 20, wherein the third spectral portion corresponds to phosphate $v_1$.

22. A method as defined in claim 21, wherein the third spectral portion is at 23 $cm^{-1}$ with a shoulder at 940 $cm^{-1}$.

23. A method as defined in claim 20, wherein the fourth spectral portion corresponds to amide I.

24. A method as defined in claim 23, wherein the fourth spectral portion corresponds to a plurality of amide I bands between 25 $cm^{-1}$ to 1700 $cm^{-1}$.

25. A method as defined in claim 20, wherein the fourth spectral portion corresponds to amide III.

26. A method as defined in claim 25, wherein the fourth spectral portion corresponds to a plurality of amide III bands.

27. An apparatus for determining bone tissue susceptibility to fracture, comprising:
   a substantially monochromatic light source;
   an optical probe optically coupled to the substantially monochromatic light source and configured to irradiate a portion of bone tissue of a patient through skin of the patient and to receive light scattered from the portion of bone tissue;
   a spectrum analyzer optically coupled to receive light received by the optical probe, the spectrum analyzer configured to generate Raman spectral content information associated with the received light; and
   a computing device communicatively coupled to the spectrum analyzer, the computing device configured to:
      measure, in the Raman spectral content information, a first ratio of a first spectral portion corresponding to amide to a second spectral portion corresponding to amide, and
      generate diagnostic information indicative of whether the patient has a bone tissue condition based at least in part on the Raman spectral content information, including the first ratio.

28. An apparatus as defined in claim 27, wherein the light source produces light having a wavelength substantially between 700 nanometers and 1100 nanometers.

29. An apparatus as defined in claim 27, wherein the computing device comprises a digital circuit.

30. An apparatus as defined in claim 27, wherein the computing device comprises an analog circuit.

31. An apparatus as defined in claim 27, wherein the computing device comprises a mixed analog and digital circuit.

32. An apparatus as defined in claim 27, wherein the computing device comprises a processor coupled to a memory.

33. An apparatus as defined in claim 27, wherein the bone tissue condition comprises at least one of a susceptibility to fracture, osteoporosis, a genetic disorder, and an acquired disorder.

34. An apparatus as defined in claim 27, wherein the computing device is configured to estimate a susceptibility to fracture of bone tissue of the patient based at least in part on the Raman spectral content information.

35. An apparatus as defined in claim 34, wherein the Raman spectral content information includes a plurality of bands corresponding to received light at one or more wavelengths;
   wherein the computing device is configured to determine at least one area or height of at least one band.

36. An apparatus as defined in claim 35, wherein the computing device is configured to fit a curve to the at least one band.

37. An apparatus as defined in claim 35, wherein the computing device is configured to determine a first area or height of at least a first band;
   wherein the computing device is configured to determine a second area or height of at least a second band; and
   wherein the computing device is configured to determine the first ratio using the first area or height and the second area or height.

38. An apparatus as defined in claim 37, wherein the computing device is configured to estimate the susceptibility to fracture based at least in part on the first ratio.

39. An apparatus as defined in claim 37, wherein the computing device is configured to determine a third area or height of at least a third band;
   wherein the computing device is configured to determine a second ratio of the third area or height and the first area or height.

40. An apparatus as defined in claim 39, wherein the computing device is configured to estimate the susceptibility to fracture based at least in part on the first ratio and the second ratio.

41. An apparatus as defined in claim 34, wherein the computing device is configured to estimate the susceptibility to fracture further based at least in part on at least one of an age of the patient, a height of the patient, a weight of the patient, a bone mineral density of the patient, and a family history of the patient.

42. An apparatus as defined in claim 27, wherein the computing device is configured to generate diagnostic information further based at least in part on at least one of an age of the patient, a height of the patient, a weight of the patient, a bone mineral density of the patient, and a family history of the patient.

43. A method for determining bone tissue susceptibility to fracture, the method comprising:
   irradiating a portion of bone tissue of a patient using a light source;
   receiving light scattered from the portion of the bone tissue;
   determining Raman spectra information from the received scattered light including measuring a ratio of a first spectral portion corresponding to amide to a second spectral portion corresponding to amide;
   determining a level of bone fracture risk of the patient based at least in part on the Raman spectra information, including the ratio, wherein the level of bone fracture risk is from a plurality of risk levels including a plurality of above-normal risk levels.

44. An apparatus for determining bone tissue susceptibility to fracture, comprising:
   a light source;
   a Raman probe to receive light scattered from a portion of bone tissue of a patient irradiated by the light source;
   a spectrum analyzer coupled to receive light received by the light receiver and to determine Raman spectra information for the received light; and
   a computing device coupled to the spectrum analyzer, the computing device configured to:
      measure, in the Raman spectra information, a ratio of a first spectral portion corresponding to amide to a second spectral portion corresponding to amide, and
      determine a level of bone fracture risk of the patient based at least in part on the Raman spectra information, including the ratio, wherein the level of bone fracture risk is from a plurality of risk levels including a plurality of above-normal risk levels.

* * * * *